United States Patent

Pallos et al.

[11] 3,970,758
[45] July 20, 1976

[54] CERTAIN GERANYL PHENYL ETHERS AND THEIR EPOXIDES AND THEIR USE IN CONTROLLING INSECTS

[75] Inventors: Ferenc M. Pallos, Pleasant Hill; Hwalin Lee, Palo Alto; Julius J. Menn, Saratoga, all of Calif.

[73] Assignee: Stauffer Chemical Company, Westport, Conn.

[22] Filed: May 19, 1975

[21] Appl. No.: 578,580

Related U.S. Application Data

[60] Division of Ser. No. 856,140, Sept. 8, 1969, Pat. No. 3,907,783, which is a continuation-in-part of Ser. No. 815,229, April 10, 1969, abandoned.

[52] U.S. Cl. ............................ 424/278; 424/276; 424/277; 424/304; 424/337; 424/340; 424/341
[51] Int. Cl.² .......................................... A01N 9/28
[58] Field of Search .................. 424/278, DIG. 12

[56] References Cited
UNITED STATES PATENTS

| | | |
|---|---|---|
| 3,711,519 | 1/1973 | Dolejs et al. .................. 424/278 |
| 3,825,602 | 7/1974 | Pallos et al. .................. 424/278 |
| 3,851,061 | 11/1974 | Lee et al. .................. 424/278 |
| 3,888,987 | 6/1975 | Pallos et al. .................. 424/278 |

*Primary Examiner*—V. D. Turner
*Attorney, Agent, or Firm*—Edwin H. Baker

[57] ABSTRACT

Compounds having the formula

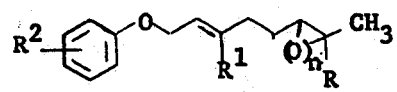

in which R and $R^1$ are independently methyl or ethyl; $n$ is the integer zero or one; $R^2$ is hydrogen, lower alkyl, lower alkenyl, lower alkoxy, halogen, nitro, lower alkylthio, or certain hetrocyclic radicals; the use of these compounds in controlling insects; and a method of preparing certain intermediates which are useful in preparing certain of the compounds.

19 Claims, No Drawings

CERTAIN GERANYL PHENYL ETHERS AND THEIR EPOXIDES AND THEIR USE IN CONTROLLING INSECTS

This application is a divisional of application Ser. No. 856,140 filed Sept. 8, 1969, now U.S. Pat. No. 3,907,783 which is a continuation-in-part of Ser. No. 815,229, filed Apr. 10, 1969, now abandoned.

This invention relates to the use of certain novel chemical compounds in controlling insects, more particularly, the chemical compounds are certain phenyl geranyl ethers and their epoxides. The invention also relates to a method of preparing certain intermediates which are useful in preparing certain of the novel compounds.

It has been found that there is a class of compounds which acts in a different manner on insects than presently used insecticides and exerts a disrupting influence upon the normal development of insects. Such compounds impede the metamorphosis of the normal pupation of pest insects and result in the formation of members of the treated species which are non-viable or sterile. This ultimately leads, indirectly at least, to the destruction of a pest population.

The compounds of the present invention are believed to have the further advantages that they are non-toxic to warm-blooded animals and highly effective to control insects at low dosages. It is also hoped that it will be more difficult for insects to develop resistance against these compounds.

One embodiment of the present invention is concerned with novel pesticidal compositions.

In another embodiment, the invention is concerned with the active pesticidal component of such compositions.

In still another embodiment, the invention is concerned with a process for controlling insects by hindering or impeding the metamorphosis and reproduction of the insects.

And in another embodiment, the invention is concerned with a process for preparing certain epoxidized compounds.

The compounds of the present invention that are useful in controlling insects are those having the formula

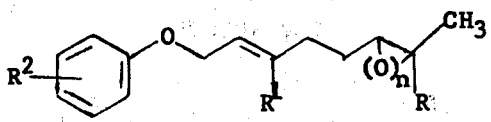

in which R and $R^1$ are independently methyl or ethyl, $n$ is the integer zero or 1, preferably 1; $R^2$ is hydrogen; halogen; lower alkyl having 1 to 6 carbon atoms, preferably 1 to 4 carbon atoms; lower alkoxy having 1 to 4 carbon atoms, preferably 1 to 2 carbon atoms; lower alkenyl, having 2 to 6 carbon atoms, preferably 3 to 4 carbon atoms; lower alkylthio having 1 to 4 carbon atoms, preferably 1 to 2 carbon atoms, nitro, or the hetrocyclic group

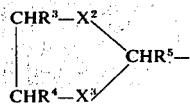

in which $X^2$ or $X^3$ is oxygen or sulfur, and $R^3$, $R^4$, or $R^5$ is hydrogen, methyl or ethyl; most preferably $R^2$ is in the para position.

Carbon atoms, joined to two or less hydrogen atoms, occupy each angle in the backbone of the compound represented by the above formula. Letters at the terminals and branches have been used to show the attached groups.

As indicated heretofore, the above compounds are useful in impeding the metamorphosis and/or the reproduction of insects. The activity of the compounds is such that insects at any stage of their development can be effectively treated therewith.

The compound having the formula

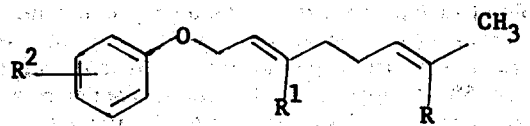

in which R, $R^1$, and $R^2$ are as defined can be prepared by the following reaction:

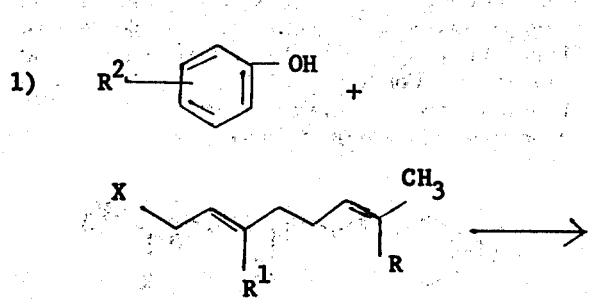

in which R, $R^1$, and $R^2$ are as defined, and X is chlorine or bromine, or iodine.

Preferably, reaction number 1 is carried out in a solvent such as 1,2-dimethoxyethane, with stirring by slowly adding an acid acceptor, such as a diluted solution of alcoholic KOH, at room temperature, followed by heating at reflux to complete the reaction. The reaction product is recovered by conventional techniques such as stripping off the solvent in vacuum, extracting the residue with ether, washing the ether phase with 10% KOH solution and then with water, followed by drying with anhydrous $MgSO_4$. Finally, the drying agent is filtered off and the ether is removed by vacuum stripping.

Preferably, reaction number 1 is carried out using equal mole amounts of the reactant, although an excess of either reactant can be used.

Compounds having the formula

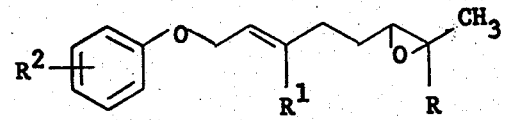

in which R and $R^1$ are as defined and $R^2$ is as defined, excluding lower alkylthio, and said hetrocyclic group when containing a sulfur atom can be prepared by the following reaction:

2) 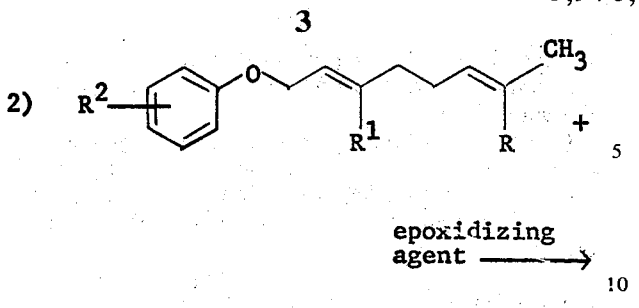

epoxidizing agent ⟶ in which R and R¹ are as defined and R² is as defined, excluding alkylthio.

Preferably, reaction number 2 is carried out in a solvent such as methylene chloride, preferably the epoxidizing agent is added slowly with stirring at a temperature sufficient to give a controlled reaction, such as about 5°C. to about 10°C. Preferably reaction number 2 is carried out using about equal mole amounts of the reactants, or with a slight excess of the epoxidizing agent. The reaction product is recovered by conventional means.

The epoxidizing agents are well-known to those skilled in the art and include such materials as meta-chloroperbenzoic acid. Reference is made to Kirk-Othmer Encyclopedia of Chemical Technology, 2nd. Edition, 1965, Vol. 8, Pages 238–244, for a discussion of various types of epoxidizing agents.

Compounds having the formula

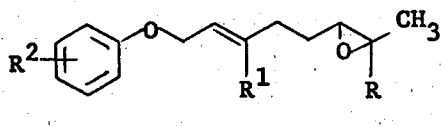

in which R and R¹ are as defined and R² is lower alkylthio, or said hetrocyclic group when it contains a sulfur atom, and can be prepared by the following reactions:

3) 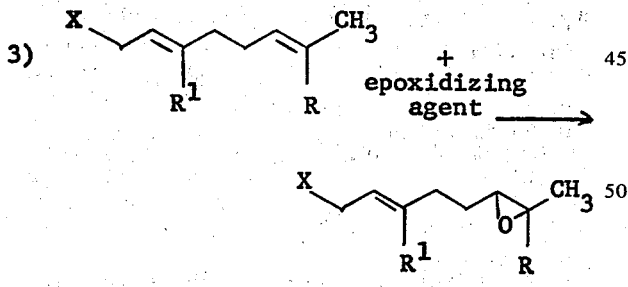
+ epoxidizing agent ⟶ in which R and R¹ are as defined, and X is chlorine or bromine, or iodine, and

4) 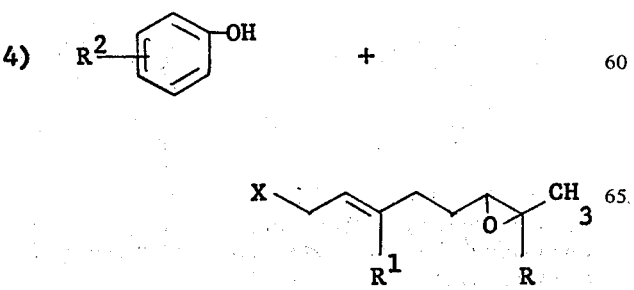

in which R and R¹ are as defined and R² is lower alkylthio, or said hetrocyclic group when it contains a sulfur atom, and X is chlorine or bromine, or iodine.

Preferably, reaction numbers 3 and 4 are carried out under the same conditions as described for reaction numbers 2 and 1, respectively.

A method of preparation for the compounds

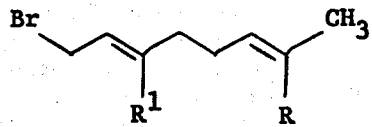

where either R or R¹ are ethyl and was published by W. S. Bowers, Gordon Research Conf., June, 1968, in a symposium entitled, BIO-CHEMISTRY AND AGRICULTURE, Tilton, N.H.

Preparation of the compounds of this invention is illustrated by the following specific examples.

EXAMPLE I

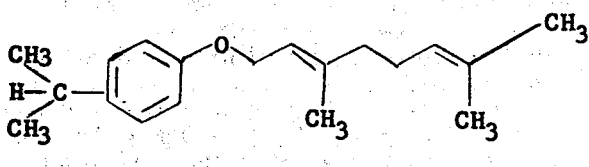

43.4 gr. (0.2 mole) geranylbromide is added to a solution of 30.0 gr. (0.22 mole) p-isopropylphenol dissolved in 220 ml. 1,2-di-methoxyethane. A solution of 14.0 gr. KOH (pellets, 85%) in 200 ml. 95% ethanol is slowly dropped in at room temperature, while the reaction flask is kept in a room-temperature waterbath during the addition. A white precipitation forms and the mixture is refluxed for two hours. The mixture is cooled, stripped in vacuum, and extracted with ether. The ether layer is washed twice with 10% KOH solution and once again with water. It is dried over anhydrous $MgSO_4$, filtered, and the solvent stripped in vacuum. 41.2 gr. of a compound corresponding to the above formula is recovered having $n_D^{30} = 1.5060$. The structure is confirmed by infrared and n.m.r. spectrascopy.

EXAMPLE II

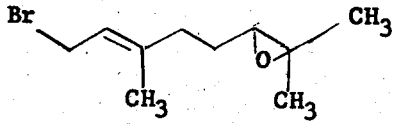

10.9 gr. (0.05 mole) geranylbromide is dissolved in 100 ml. methylene chloride. A stoichiometric amount of metachloroperbenzoic acid in methylenechloride is added at 5°C. under stirring. After addition, the mixture is stirred at room temperature overnight. The reaction product is washed three times with 10% $NaHCO_3$ solution, dried with anhydrous $MgSO_4$, filtered, and stripped. 9.8 gr. of a compound corresponding to the above formula is recovered having a $n_D^{30}=1.6910$. The structure is confirmed by the IR and n.m.r. spectrascopy.

EXAMPLE III

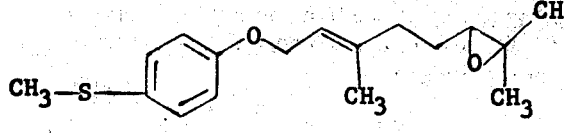

0.28 gr. (0.002 mole) p-(methylthio) phenol is dissolved in 3 ml. tetrahydrofuran. 2.0 ml. of a 1 mole KOH solution in 95% ethanol is added and 0.5 gr. (0.002 mole) of the compound prepared in Example II, dissolved in 5 ml. tetrahydrofuran, is added. After stirring at room temperature for one hour, 30 ml. ether is added, and the mixture transferred in a separatory funnel. The mixture is washed once with 10% $Na_2CO_3$ solution and once with water, then dried over anhydrous $MgSO_4$. It is then filtered and stripped to yield 0.4 gr. of a compound corresponding to the above formula. The structure is confirmed by IR and n.m.r. spectroscopy.

The following is a Table of certain selected compounds that are preparable according to the procedures described hereto. Compound numbers are assigned to each compound and are used throughout the remainder of the specification.

TABLE I

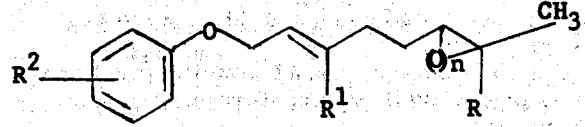

| COMPOUND NUMBER | R | R$^1$ | n | R$^2$ |
|---|---|---|---|---|
| 1 | $CH_3$ | $CH_3$ | zero | H |
| 2 | $CH_3$ | $CH_3$ | zero | 4-$CH_3$ |
| 3 | $CH_3$ | $CH_3$ | zero | 4-i-$C_3H_7$ |
| 4 | $CH_3$ | $CH_3$ | zero | 4-$NO_2$ |
| 5 | $CH_3$ | $CH_3$ | zero | 3-Cl |
| 6 | $CH_3$ | $CH_3$ | zero | 4-Cl |
| 7 | $CH_3$ | $CH_3$ | zero | 4-Br |
| 8 | $CH_3$ | $CH_3$ | zero | 4-I |
| 9 | $C_2H_5$ | $C_2H_5$ | zero | 4-$CH_3S$— |
| 10 | $CH_3$ | $CH_3$ | zero | 4-CN |
| 11 | $CH_3$ | $CH_3$ | zero | 4-sec-$C_4H_9$ |
| 12 | $CH_3$ | $CH_3$ | zero | 3-$CH_3O$ |
| 13 | $CH_3$ | $CH_3$ | zero | 4-$CH_3O$— |
| 14 | $CH_3$ | $CH_3$ | zero | 4-$C_2H_5O$— |
| 15 | $C_2H_5$ | $CH_3$ | zero | 4-n-$C_4H_9O$ |
| 16 | $CH_3$ | $CH_3$ | zero | 4-$CH_3S$— |
| 17 | $CH_3$ | $CH_3$ | zero | 4-$C_2H_5$— |
| 18 | $CH_3$ | $C_2H_5$ | zero | 4-i-$C_3H_7$— |
| 19 | $CH_3$ | $CH_3$ | zero | 4-$CH_3$—CH=C($CH_3$) |
| 20 | $CH_3$ | $CH_3$ | zero | 4-$CH_3$—CH=CH— |
| 21 | $CH_3$ | $CH_3$ | 1 | H |
| 22 | $CH_3$ | $CH_3$ | 1 | 4-$CH_3$ |
| 23 | $CH_3$ | $CH_3$ | 1 | 4-i-$C_3H_7$ |
| 24 | $CH_3$ | $CH_3$ | 1 | 4-$NO_2$ |
| 25 | $CH_3$ | $CH_3$ | 1 | 3-Cl |
| 26 | $CH_3$ | $CH_3$ | 1 | 4-Cl |
| 27 | $CH_3$ | $CH_3$ | 1 | 4-Br |
| 28 | $CH_3$ | $CH_3$ | 1 | 4-I |
| 29 | $CH_3$ | $CH_3$ | 1 | 4-F |
| 30 | $CH_3$ | $CH_3$ | 1 | 4-CN |
| 31 | $CH_3$ | $CH_3$ | 1 | 3-$CH_3O$— |
| 32 | $CH_3$ | $CH_3$ | 1 | 4-$CH_3O$— |
| 33 | $CH_3$ | $CH_3$ | 1 | 4-$C_2H_5O$— |
| 34 | $C_2H_5$ | $C_2H_5$ | 1 | 4-$CH_3S$— |
| 35 | $CH_3$ | $CH_3$ | 1 | 4-n-$C_4H_9$— |
| 36 | $CH_3$ | $CH_3$ | 1 | 4-$CH_3$—S— |
| 37 | $CH_3$ | $CH_3$ | 1 | 4-$C_2H_5$ |
| 38 | $C_2H_5$ | $CH_3$ | 1 | 4-i-$C_3H_7$ |
| 39 | $C_2H_5$ | $C_2H_5$ | 1 | 4-$CH_3$— CH=C($CH_3$) |
| 40 | $CH_3$ | $CH_3$ | 1 | 4-$CH_3$—CH=CH |
| 41 | $CH_3$ | $CH_3$ | 1 | 4-$CH_3$—$CH_2$—CH($CH_3$) |
| 42 | $CH_3$ | $CH_3$ | 1 | 4-n-$C_3H_7$ |
| 43 | $CH_3$ | $CH_3$ | 0 | 3-$C_2H_5$ |
| 44 | $CH_3$ | $CH_3$ | 1 | 3-$C_2H_5$ |
| 45 | $CH_3$ | $CH_3$ | 1 | 4-$\begin{matrix}CH_2-S\\ \\ CH_2-S\end{matrix}\Big\rangle CH-$ |

INSECTICIDAL EVALUATION TEST

The degree of activity of a candidate compound to hinder or impede the metamorphosis of insects is measured by treating the penultimate larval stage of a representative insect with the compound and examining it after its last molt toward the adult form for retention of immature features.

Specifically, yellow mealworm, Tenebrio molitor, L., larvae are maintained at 28°C. and 40% humidity on a diet of bran flakes. Prepupae are collected from the culture and kept in separate containers. The pupae collected once daily, are 1–25 hours old at the time of treatment. By means of a syringe, suitable amounts of candidate compounds in 0.5 or 1.0 $\mu l$ of acetone are applied to the venter of Tenebrio molitor, L. pupae. Treated pupae are maintained at 28°C. and 40% humidity until the adults emerged (usually within 6–8 days). Emerged adults are graded as positive, negative, or dead. To be considered a positive response, the presence of typical pupal cuticle, urogomphi, gin trap, and abnormal wings, etc. are required. For each test, 2 groups of 20 pupae were used and the averaged results were reported.

The dose of a candidate compound per pupa that is needed to kill or give a positive response in the above insecticidal evaluation test for 10 of the 20 pupae is determined. Table II shows these doses under the column $ED_{50}$.

TABLE II

| COMPOUND NUMBER | $ED_{50}$-ug/pupa |
|---|---|
| 1 | 40 |
| 2 | <50 |
| 3 | 1 |
| 4 | 30 |
| 5 | >50 |
| 6 | 1 |
| 7 | 1 |
| 8 | 5 |
| 10 | >50 |
| 11 | 2 |
| 12 | 4 |
| 13 | 1 |
| 14 | <50 |
| 16 | 0.2 |
| 17 | 0.1 |
| 21 | 5 |
| 22 | 0.07 |
| 23 | 0.02 |
| 24 | 3 |
| 25 | 30 |

TABLE II-continued

| COMPOUND NUMBER | ED$_{50}$-ug/pupa |
|---|---|
| 26 | 0.1 |
| 27 | <0.5 |
| 28 | <0.5 |
| 30 | 50 |
| 31 | 0.7 |
| 32 | 0.08 |
| 33 | 0.3 |
| 35 | >50 |
| 36 | 0.01 |
| 37 | 0.0025 |
| 41 | 0.1 |
| 42 | 0.1 |
| 43 | 8.0 |
| 44 | 1.0 |
| 45 | 0.08 |

The compounds of this invention are generally embodied into a form suitable for convenient application. For example, the compounds can be embodied into pesticidal composition which are provided in the form of emulsions, suspensions, solutions, dusts, and aerosol sprays. In general, such compositions will contain, in addition to the active compound, the adjuvants which are found normally in pesticide preparations. In these compositions, the active compounds of this invention can be employed as the sole pesticide component or they can be used in admixture with other compounds having similar utility. The pesticide compositions of this invention can contain, as adjuvants, organic solvents, such as sesame oil, xylene range solvents, heavy petroleum, etc.; water; emulsifying agents; surface active agents; talc; pyrophyllite; diatomite; gypsum; clays; propellants, such as dichlorodifluoromethane, etc. If desired, however, the active compounds can be applied directly to feedstuffs, seeds, etc. upon which the pests feed. When applied in such a manner, it will be advantageous to use a compound which is not volatile. In connection with the activity of the presently disclosed pesticidal compounds, it should be fully understood that it is not necessary that they be active as such. The purposes of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid composition, for example, an emulsion, suspension, or aerosol spray. While the concentration of the active pesticide in the present compositions can vary within rather wide limits, ordinarily the pesticide compound will comprise not more than about 15.0% by weight of the composition. Preferably, however, the pesticide compositions of this invention will be in the form of solutions or suspensions containing about 0.1 to 1.0% by weight of the active pesticide compound.

What is claimed is:

1. A method of controlling Tenebrio molitor comprising applying thereto at any stage of their development a metamorphosis hindering amount of a compound of the formula:

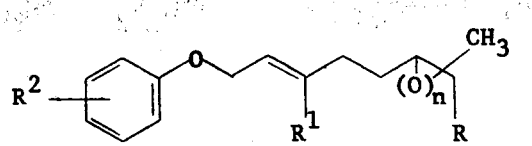

in which R and $R^1$ are independently methyl or ethyl; $n$ is the integer 1; $R^2$ is hydrogen, halogen, lower alkyl having 1 to 6 carbon atoms, lower alkoxy having 1 to 4 carbon atoms, lower alkenyl having 2 to 6 carbon atoms, lower alkylthio having 1 to 5 carbon atoms, or nitro.

2. The method of claim 1 in which R and $R^1$ are methyl; $n$ is 1; and $R^2$ is lower alkyl having 1 to 4 carbon atoms.

3. The method of claim 1 in which R and $R^1$ are methyl; $n$ is 1; and $R^2$ is lower alkoxy having 1 to 2 carbon atoms.

4. The method of claim 1 in which R and $R^1$ are methyl; $n$ is 1; and $R^2$ is lower alkylthio having 1 to 2 carbon atoms.

5. The method of claim 1 in which R and $R^1$ are methyl; $n$ is 1; and $R^2$ is halogen.

6. The method of claim 2 in which $R^2$ is 4-methyl.

7. The method of claim 2 in which $R^2$ is 4-i-propyl.

8. The method of claim 3 in which $R^2$ is 4-methoxy.

9. The method of claim 4 in which $R^2$ is 4-methylthio.

10. The method of claim 2 in which $R^2$ is 4-ethyl.

11. The method of claim 1 in which R and $R^1$ are ethyl; $n$ is 1; and $R^2$ is lower alkyl having 1 to 4 carbon atoms.

12. The method of claim 1 in which R and $R^1$ are ethyl; $n$ is 1; and $R^2$ is lower alkoxy having 1 to 2 carbon atoms.

13. The method of claim 1 in which R and $R^1$ are ethyl; $n$ is 1; and $R^2$ is lower alkylthio having 1 to 2 carbon atoms.

14. The method of claim 1 in which R and $R^1$ are ethyl; $n$ is 1; and $R^2$ is halogen.

15. The method of claim 11 in which $R^2$ is 4-methyl.

16. The method of claim 11 in which $R^2$ is 4-i-propyl.

17. The method of claim 12 in which $R^2$ is 4-methoxy.

18. The method of claim 13 in which $R^2$ is 4-methylthio.

19. The method of claim 11 in which $R^2$ is 4-ethyl.

* * * * *